US007088115B1

(12) United States Patent
Glenn et al.

(10) Patent No.: US 7,088,115 B1
(45) Date of Patent: Aug. 8, 2006

(54) ELECTROCHEMICAL IMPEDANCE SPECTROSCOPY SYSTEM AND METHODS FOR DETERMINING SPATIAL LOCATIONS OF DEFECTS

(75) Inventors: David F. Glenn, Idaho Falls, ID (US); Gretchen E. Matthern, Idaho Falls, ID (US); W. Alan Propp, Idaho Falls, ID (US); Anne W. Glenn, Idaho Falls, ID (US); Peter G. Shaw, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 11/015,427

(22) Filed: Dec. 16, 2004

(51) Int. Cl.
*G01R 27/08* (2006.01)
*G01B 5/30* (2006.01)

(52) U.S. Cl. .................. 324/691; 324/718; 702/35

(58) Field of Classification Search ........... 324/691, 324/649, 600, 452, 456, 216, 237, 238, 240, 324/713, 715, 718, 71.1; 702/35, FOR. 125; 73/598, 600
See application file for complete search history.

(56) References Cited

U.S. PATENT DOCUMENTS

| 4,835,466 | A * | 5/1989 | Maly et al. .................. 324/537 |
| 6,151,969 | A * | 11/2000 | Miller et al. ................ 73/808 |
| 6,339,334 | B1 * | 1/2002 | Park et al. .................. 324/425 |
| 6,466,881 | B1 * | 10/2002 | Shih et al. .................. 702/84 |
| 6,784,672 | B1 * | 8/2004 | Steele et al. ................ 324/663 |
| 6,911,828 | B1 * | 6/2005 | Brossia et al. .............. 324/649 |
| 2003/0009300 | A1 * | 1/2003 | Giurgiutiu .................... 702/35 |
| 2004/0091759 | A1 * | 5/2004 | Harrington et al. ........... 429/22 |
| 2004/0212370 | A1 * | 10/2004 | Cunningham et al. ....... 324/446 |
| 2005/0114045 | A1 * | 5/2005 | Giurgiutiu et al. ............ 702/35 |
| 2005/0287402 | A1 * | 12/2005 | Maly et al. .................... 429/13 |

OTHER PUBLICATIONS

Adrian W. Bott, PH.D., "Electrochemical Impedance Spectroscopy Using the BAS-Zahner IM6 and IM6e Impedance Analyzers", Current Separations 17:2 (1998), pp. 53-54.
Guangling Song, "Equivalent circuit model for AC electrochemical impedance spectroscopy of concrete", Cement and Concrete Research, (2000), pp. 1724-1730.
G.D. Davis, L.A. Krebs, and C.M. Dacres, "Detection of Moisture in Composites Using An Electrochemical Impedance Spectroscopy Sensor", DACCO SCI News and Highlights, Apr. 25, 2000, www.daccosci com/ Aging_Aircraft_Alberq.htm, pp. 1-13.

(Continued)

*Primary Examiner*—Anjan Deb
*Assistant Examiner*—Hoai-An D. Nguyen
(74) *Attorney, Agent, or Firm*—Wells St. John P.S.

(57) ABSTRACT

A method and apparatus for determining spatial locations of defects in a material are described. The method includes providing a plurality of electrodes in contact with a material, applying a sinusoidal voltage to a select number of the electrodes at a predetermined frequency, determining gain and phase angle measurements at other of the electrodes in response to applying the sinusoidal voltage to the select number of electrodes, determining impedance values from the gain and phase angle measurements, computing an impedance spectrum for an area of the material from the determined impedance values, and comparing the computed impedance spectrum with a known impedance spectrum to identify spatial locations of defects in the material.

12 Claims, 8 Drawing Sheets

OTHER PUBLICATIONS

Federal Highways Administration—Geophysical Imaging Resource Site, "Rebar Quality and Bonding to Concrete Within Concrete Element . . .", www/cflhd/agm/engApplications/BridgeSystemSubstructure/23RebarQuality. . . , pp. 1-3.

* cited by examiner

FIG. 6

ELECTROCHEMICAL IMPEDANCE SPECTROSCOPY SYSTEM AND METHODS FOR DETERMINING SPATIAL LOCATIONS OF DEFECTS

GOVERNMENT RIGHTS

The United States Government has rights in the following invention pursuant to Contract No. DE-AC07-99ID13727 between the United States Department of Energy and Bechtel BWXT Idaho, LLC.

TECHNICAL FIELD

Aspects of the invention generally relate to electrochemical impedance spectroscopy system and method for quality control to visualize locations of anomalies in solid and semi-solid phase conductive materials such as, for example, concrete.

BACKGROUND OF THE INVENTION

Concrete is a widely used construction material. As with all construction materials, improved quality is desired for the performance of a finished structure. Existing field quality control techniques for concrete such as, for example, slump test, are used to monitor bulk physical properties. Such quality control techniques, however, do not directly measure the individual physical or chemical components that affect the performance of the concrete material. Microstructure of concrete can be of considerable importance as it can govern the mechanical properties and durability of the concrete. Such microstructure can have significant influences on corrosion performance of reinforcing steel in the concrete.

Current methods for measuring performance of concrete are generally implemented after the material has been poured and allowed to set. Under such conditions, corrections to the material can be difficult to implement. A technique that could quantify the quality of cements in the field prior to pouring could save time and money.

Electrochemical impedance spectroscopy (EIS) has been demonstrated to characterize electrochemical properties of materials and their interfaces. Electrochemical impedance spectroscopy is generally described in U.S. Pat. No. 5,370,776 to Chen, U.S. Pat. No. 5,425,867 to Dawson et al., and U.S. Pat. No. 6,151,969 to Miller et al., all of which are incorporated by reference in their entirety in this patent.

It would be desirable to have, in some embodiments, a non-invasive system and method using the electrochemical impedance spectroscopy to determine composition of a material to overcome the above-identified drawbacks, in some embodiments. It would also be desirable to use electrochemical impedance spectroscopy to measure a variety of other physical phenomenon and overcome the time and expense involved in measuring each of such physical phenomenon.

SUMMARY OF THE INVENTION

A need exists to use the electrochemical impedance spectroscopy to interrogate a system of interest in order to non-invasively determine a composition of the system. Needs also exist to non-invasively determine the integrity of a structure, weight of an object, or the speed of a vehicle using the principles of electrochemical impedance spectroscopy.

Aspects of the invention generally relate to electrochemical impedance spectroscopy systems and methods for quality control to visualize locations of anomalies in solid and semi-solid phase conductive materials such as, for example, concrete. Aspects of the invention also relate to methods and systems for determining a composition of a concrete material, methods and systems for monitoring the stability of a bridge structure, methods and systems for determining the weight of an object, and methods and systems for determining the speed of a vehicle.

In some embodiments, a method and apparatus for determining spatial locations of defects in a material are provided. The method includes providing a plurality of electrodes in contact with a material, applying a sinusoidal voltage to a select number of the electrodes at a predetermined frequency, determining gain and phase angle measurements at other of the electrodes in response to applying the sinusoidal voltage to the select number of electrodes, determining impedance values from the gain and phase angle measurements, computing an impedance spectrum for an area of the material from the determined impedance values, and comparing the computed impedance spectrum with a known impedance spectrum to identify spatial locations of defects in the material.

In other embodiments, a system and method for determining a composition of a concrete material is described. A plurality of electrodes is configured to be placed in contact with the concrete material, the electrodes being spaced from each other. A voltage source is configured to apply a sinusoidal voltage at a predetermined frequency to a select number of the electrodes, and a current measuring device is coupled to other electrodes to measure a current response in response to applying the sinusoidal voltage. A processor is configured to determine impedance measurements using the applied sinusoidal voltage and the measured current response, compute an impedance spectrum from the impedance measurements, and compare the impedance spectrum with a known impedance spectrum to determine percentages of concrete, sand, gravel, and water in the concrete material.

In further embodiments, a method of monitoring the stability of a bridge structure includes providing a plurality of spaced apart electrodes in contact with the bridge structure, applying a voltage to a select number of the electrodes, the voltage being applied at a predetermined frequency, measuring a current response at other of the electrodes in response to applying the voltage, determining impedance measurements using the applied voltage and the measured current response, computing an impedance spectrum from the impedance measurements, and analyzing the computed impedance spectrum relative to a known impedance spectrum to identify defects of the bridge structure so as to determine the stability of the bridge structure.

In other embodiments, a system for monitoring the stability of a bridge structure includes a plurality of spaced apart electrodes configured to be placed in contact with the bridge structure, a voltage source configured to apply a voltage at a predetermined frequency to a select number of the electrodes, and a current measuring device configured to measure a current response at other of the electrodes in response to applying the voltage. The system also includes a processor configured to determine impedance measurements using the applied voltage and the measured current response, compute an impedance spectrum from the impedance measurements, and analyze the computed impedance spectrum relative to a known impedance spectrum to identify defects of the bridge structure so as to determine the stability of the bridge structure.

In other embodiments, a method of determining the weight of an object includes providing the object on a concrete structure, providing a plurality of spaced apart electrodes in contact with the concrete structure, applying a sinusoidal voltage to select ones of the electrodes at a predetermined frequency, measuring a current response at other of the electrodes in response to applying the sinusoidal voltage, determining impedance measurements, of the concrete structure with the object on the concrete structure, using the applied sinusoidal voltage and the measured current response, computing an impedance spectrum from the impedance measurements, and analyzing the computed impedance spectrum with known impedance spectra for differing weights to determine the weight of the object provided on the concrete structure.

In yet other embodiments, a system for determining the weight of an object includes a plurality of spaced apart electrodes configured to be in contact with a concrete structure having a weight thereon, a voltage source configured to apply a sinusoidal voltage to at least one of the electrodes at a predetermined frequency, a current source configured to measure a current response at other of the electrodes in response to applying the sinusoidal voltage. The system also includes a processor configured to determine impedance measurements of the concrete structure, with the object on the concrete structure, using the applied sinusoidal voltage and the measured current response, compute an impedance spectrum from the impedance measurements, and analyze the computed impedance spectrum with known impedance spectra for differing weights to determine the weight of the object provided on the concrete structure.

In further other embodiments, a method of determining the speed of a vehicle includes contacting a first pair of spaced apart electrodes with a concrete structure at a first location, contacting a second pair of spaced apart electrodes with the concrete structure at a second location, the first and second locations being separated by a predetermined distance, applying a sinusoidal voltage to one of the electrodes of both the first and second pairs of electrodes at a predetermined frequency, causing the vehicle to move on the concrete structure, determining impedance measurements at the first and second locations of the concrete structure and in response to applying the sinusoidal voltage, comparing the determined impedance measurements with known impedance measurements of the concrete structure without the vehicle moving on the concrete structure, monitoring impedance variations at the first and second locations from the comparison, recording first and second time instants for the monitored impedance variations at the first and second locations, respectively, determining an elapsed time period between the first and second time instants, and computing the speed of the vehicle using the elapsed time period and the predetermined distance between the first and second locations.

In other embodiments, an electrochemical impedance spectroscopy system configured to determine the speed of a vehicle moving on a solid structure includes a first set of opposing electrodes disposed to contact a solid structure at a first location, a second set of opposing electrodes disposed to contact the solid structure at a second location, the first and second sets of electrodes being separated by a predetermined distance, and a voltage source configured to supply voltage to a select number of electrodes of the first and second sets of electrodes at a predetermined frequency. The system also includes a processor configured to determine impedance measurements at the first and second locations in response to applying the voltage to the select number of electrodes of first and second sets of electrodes, compare the determined impedance measurements with known impedance measurements of the solid structure without the vehicle moving on the solid structure, monitor impedance variations at the first and second locations from the comparison, record first and second time instants for the monitored impedance variations at the first and second locations, respectively, determine an elapsed time period between the first and second time instant, and compute the speed of the vehicle using the elapsed time period and the predetermined distance between the first and second locations.

BRIEF DESCRIPTION OF THE DRAWINGS

Preferred embodiments of the invention are described below with reference to the following accompanying drawings.

FIG. 3 shows a representative impedance plot using electrochemical impedance spectroscopy to determine differences in the concentration of coarse aggregate in fresh concrete material in accordance with one embodiment of the invention.

FIG. 5 shows a representative impedance plot for different sections of a concrete material sample to detect differences in gravel concentration in fully cured concrete in accordance with one embodiment of the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1A:
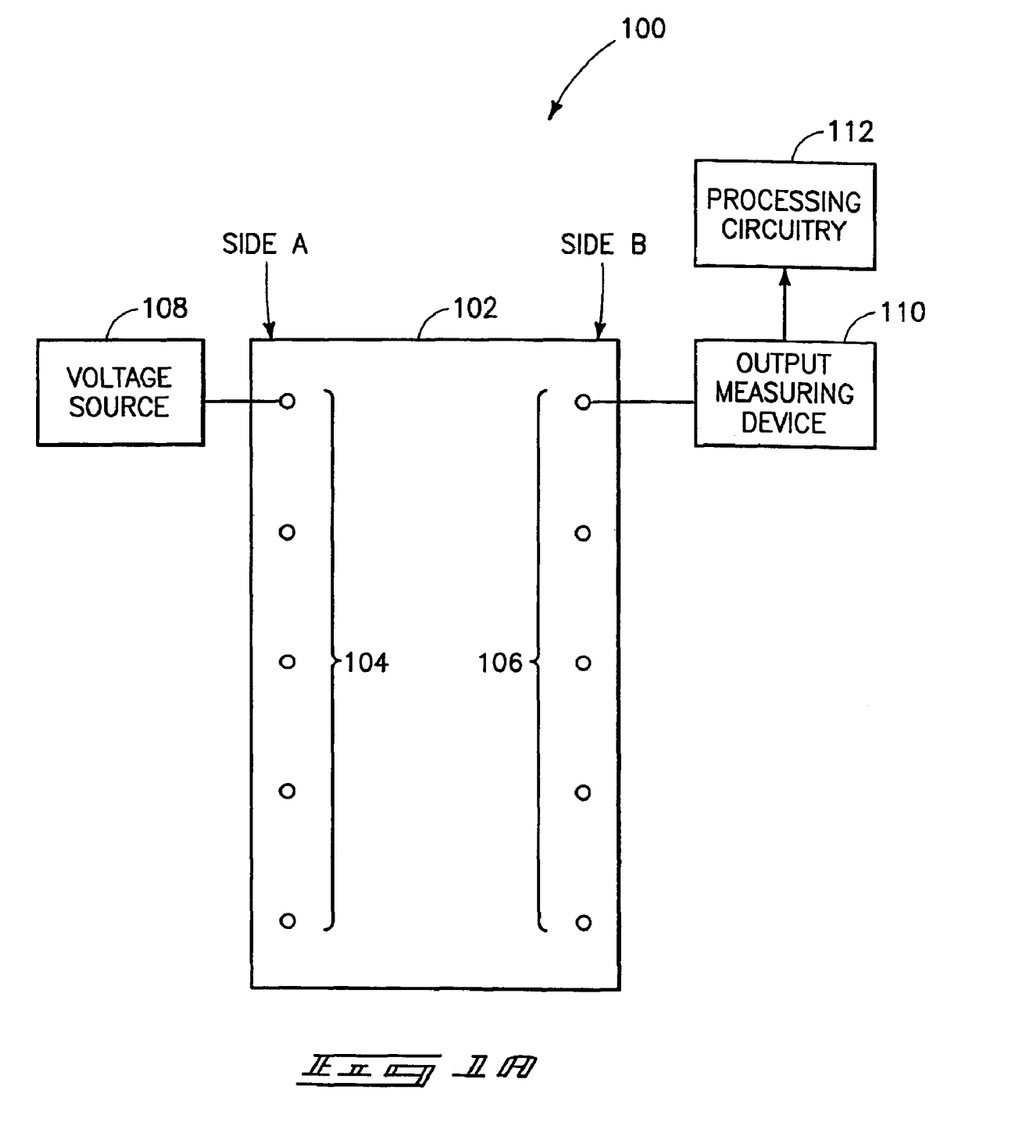
FIG. 1A is a schematic view of a data acquisition and analysis system for conducting the electrochemical impedance analysis in accordance with various embodiments of the invention.

FIG. 1A is a schematic view of a data acquisition and analysis system 100 for conducting the electrochemical impedance analysis in accordance with various embodiments of the invention. System 100 includes a material sample 102 (e.g., concrete) having a plurality of electrodes 104, 106 provided in contact with the sample 102, a voltage source 108, an output measuring device 110, and a processing circuitry 112. The sample 102 can be any solid or semi-solid conductive material.

System 100 can be used as a diagnostic tool to determine the stability of concrete structures in the field. System 100 can also be used during construction to find voids, to find poor distribution of aggregate, to monitor curing of concrete, and to continuously monitor performance and to diagnose problems (e.g., excessive vibration, etc.) in concrete structures.

The sample 102 can be a sample of fresh (e.g., uncured) concrete material in one embodiment, and it can be a sample of cured concrete material in other embodiments. The plurality of electrodes 104, 106 can be metal electrodes provided in contact with the sample 102. In one case, the plurality of electrodes 104 are provided on one side (e.g., side A) and the plurality of electrodes 106 are provided on the other side (e.g., side B) of the sample 102. The electrodes 104 can be considered to be a first array or a first set of electrodes and the electrodes 106 can be considered to be a second array or a second set of electrodes. The electrodes 104 and 106 are equally spaced on side A and side B, respectively, of the sample 102.

The voltage source 108 can be configured to provide an AC potential to the sample 102 via electrodes 104. A small amplitude AC potential is applied by the voltage source 108 to one of the electrodes 104 buried on side A of the sample 102 in order to determine an impedance spectrum for an area of the sample 102. The amplitude and phase of the resulting source current with respect to the applied source voltage is detected at one of the electrodes 106 that is provided directly across on side B of the sample 102 for each of a plurality of source signal frequencies. The resulting current can be detected by an output measuring device 110. In one case, the output measuring device 110 can be a current measuring device, such as, for example, an ammeter. Other current measuring devices can be used. The source signal frequencies are selected from a range of about 1 MHz to about 10 MHz. The shape, slope, inflection points, and the range of frequency response depend on the physical and chemical characteristics of the sample (e.g., sample 102) under evaluation. The total electrical current passing through the concrete sample is assumed to be controlled by an equivalent circuit. An exemplary equivalent circuit is discussed in an article by Song et al., entitled "Equivalent Circuit Model for AC Electrochemical Impedance Spectroscopy of Concrete," *Cement and Concrete Research*, Aug. 7, 1990.

The amplitude and phase data for the resulting current at each frequency and applied potential are used to calculate the impedance for each frequency, including both the amplitude and phase of that impedance. Impedance spectra for other sections of the sample 102 are determined by applying a signal voltage to other electrodes 104 and measuring the resulting current at electrodes 106. An impedance spectrum for the entirety of the sample 102 is then computed. The complex impedance calculations and the computing of the complete impedance spectrum can be performed under computer control.

The processing circuitry 112 can be configured to perform the impedance calculations for the resulting source current with respect to each of the supplied voltages. The processing circuitry 112 can be configured to display the complete impedance spectrum of the sample 102 so that various impedance values across various sections of the sample 102 can be manually observed to determine the composition of the sample 102. For example, one skilled in the art can manually observe the variations in impedance values across various sections of the sample and make a determination regarding the composition of the sample 102. For example, the sample 102 can include gravel, sand, cement, water, etc. and the impedance spectrum can be used to determine the composition of such materials. Based on the analysis of the impedance measurements (e.g., increase/decrease in impedance at specific frequencies), a determination of the location/ distribution of aggregate, voids, cracks, and other anomalies of a material sample (e.g., sample 102) can be made.

System 100 can be used to visualize the spatial location of material interfaces in a material sample (e.g., sample 102). The material interfaces can result from different physical properties (e.g., bulk material, aggregate, debris, voids, etc.). Quantification of specific spectral properties (e.g., impedance spectra) can be directly correlated with material type and location of anomalies such as, for example, inhomogeneity of aggregate within a bulk material sample.

In another embodiment, the processing circuitry 112 can also configured to automatically determine the composition of the sample 102 by comparing the impedance spectrum with a predetermined impedance spectrum. The processing circuitry 112 can also be configured to determine the weight of an object received on a cured concrete sample in one embodiment. In another embodiment, the processing circuitry 112 can be configured to determine the speed of an object moving across the cured concrete sample of a predetermined length. Further details of the processing circuitry 112 are set forth with respect to FIG. 2.

Figure 1B:
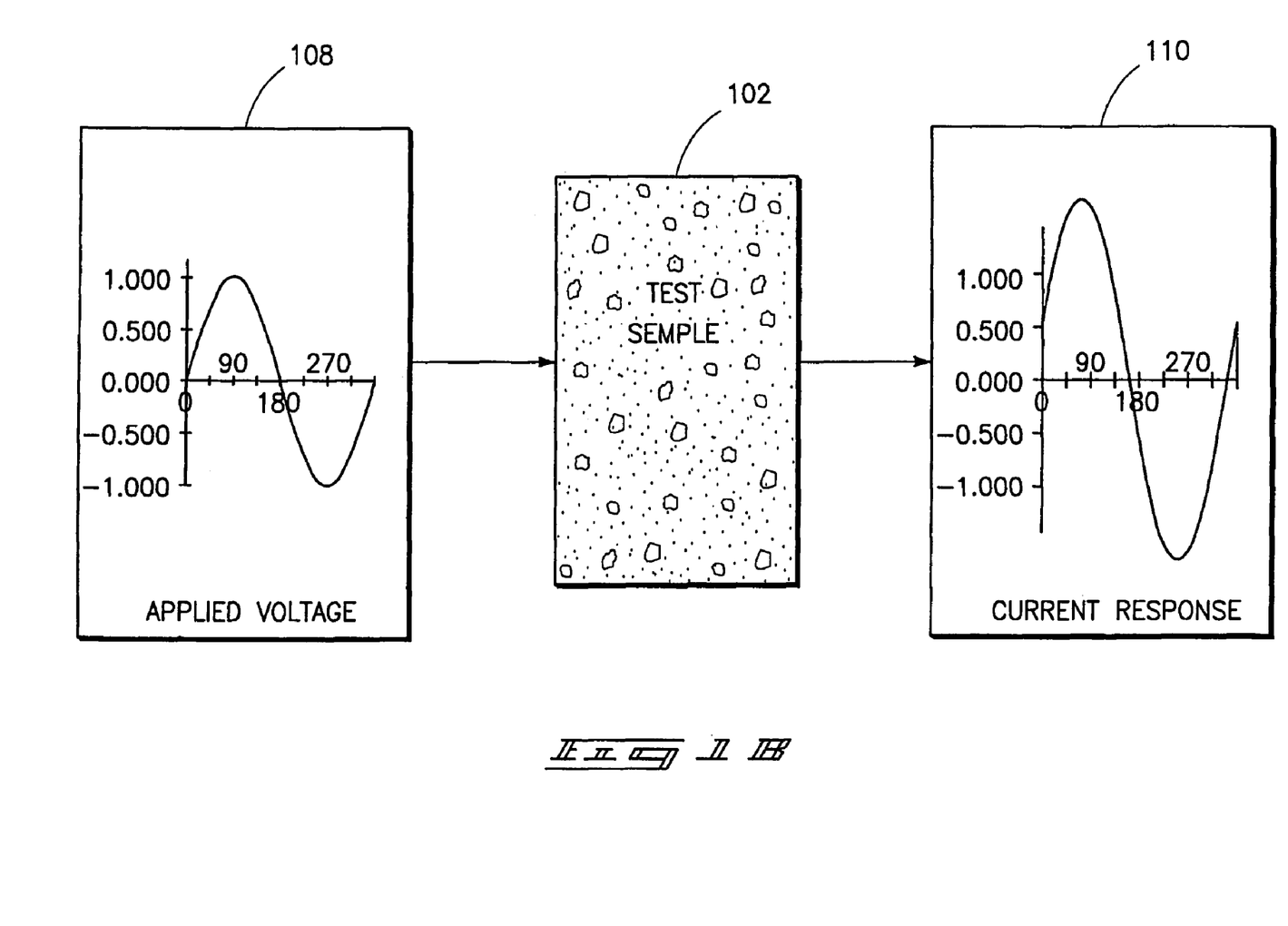
FIG. 1B is a schematic of a fundamental approach of electrochemical impedance spectroscopy in accordance with various embodiments of the invention.

FIG. 1B is a schematic of a fundamental approach of electrochemical impedance spectroscopy in accordance with various embodiments of the invention. A voltage source 108 is configured to supply a voltage to the sample 102 and the resulting current is measured using an output measuring device 110. Such details were described above with respect to FIG. 1A and therefore are not repeated.

Figure 2:
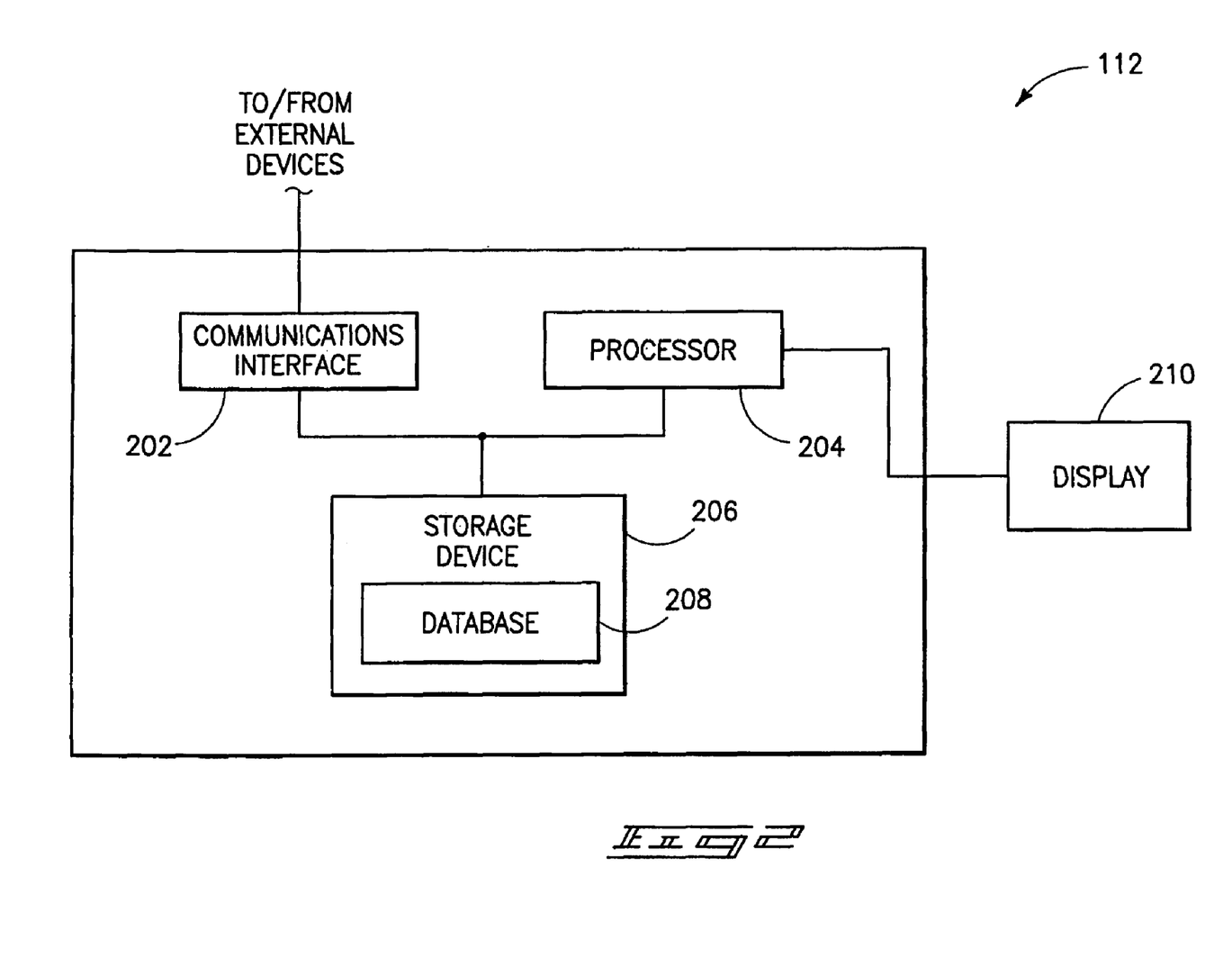
FIG. 2 is a schematic of a processing circuitry shown in FIG. 1A.

FIG. 2 is an exemplary functional block diagram of the processing circuitry 112 associated with the concrete sample 102 (FIG. 1A) in accordance with some embodiments of the invention. The processing circuitry 112 includes a communications interface 202, a processor 204, and a storage device 206 having a database 208.

The communications interface 202 can be configured to communicate electronic data externally of the processing circuitry 112, for example, with respect to the output measuring device 110 (FIG. 1A). In some embodiments, the communications interface 202 may be configured to measure the resulting current and compute impedance spectra without a need for the measuring device 110. The communications interface 202 may comprise a parallel port, USB port, EIO slot, network interface card, and/or other appropriate configuration capable of communicating electronic data.

The processor 204 can be configured to process data to compute impedance measurements and spectra (e.g., receive resulting current measurements with respect to applied signal voltages) in order to determine the composition of a concrete material sample (e.g., sample 102), to determine the weight of an object received by the sample 102, or to determine the speed of a vehicle passing on a concrete structure (e.g., sample 102) of a predetermined length. The processor 204 can be configured to determine such parameters based on predetermined values and logic stored in the storage device 206.

In one embodiment, the processor 204 may comprise circuitry configured to execute computer software code. For example, the processor 204 may be implemented as a microprocessor or other structure configured to execute executable instructions of programming including, for example, software and/or firmware instructions. Other exemplary embodiments of the processor 204 include hardware logic, PGA, FPGA, ASIC, and/or other structures. These examples of the processor 204 are for illustration, and other configurations are possible for implementing operations discussed herein.

The storage device 206 may be configured to store electronic data, file systems having one or more electronic files, programming such as executable instructions (e.g., software and/or firmware), and/or other digital information and may include processor-usable media. Processor-usable media includes any article of manufacture that can contain, store, or maintain programming, data and/or digital information for use by or in connection with an instruction execution system including processing circuitry in the exemplary embodiment. For example, exemplary processor-usable media may include any one of physical media such as electronic, magnetic, optical, electromagnetic, and infrared or semiconductor media. Some more specific examples of processor-usable media include, but are not limited to, a portable magnetic computer diskette, such as a floppy diskette, zip disk, hard drive, random access memory, read only memory, flash memory, cache memory, and/or other configurations capable of storing programming, data, or other digital information.

The storage device 206 includes a database 208 that can be stored with information for determining the composition of the sample 102 (FIG. 1A). Such information can include, for example, the impedance values and impedance spectra and composition values corresponding to such impedance values and impedance spectra. Upon determining the impedance spectra using the resulting current as described above, such impedance spectra may be correlated with the impedance spectra stored in the database 208 in order to determine the composition of the sample 102.

The database 208 can also be stored with information to determine the weight of an object received by the sample 102. For example, the database 208 can be stored with various impedance spectra corresponding to various weights. Upon determining the impedance spectra, such can be compared with the impedance spectra stored in the database 208 in order to determine the weight of an object received by the sample 102 in accordance with some embodiments.

Information processed by the processing circuitry 112 can be displayed on a display device 210. Information can be displayed in one of a textual or graphical representation. Such displayed information can include percentages of concrete, sand, gravel, and water in the material (e.g., concrete).

FIG. 3 shows a representative impedance plot using electrochemical impedance spectroscopy to determine differences in the concentration of coarse aggregate present in a test sample (e.g., sample 102 or fresh concrete material) in accordance with one embodiment of the invention. The impedance spectra of FIG. 3 can be compared with known impedance spectra of a similar sample in order to determine the composition of the test sample, thereby enabling one to discern the differences in the concentration of coarse aggregate in the test sample.

Figure 4:
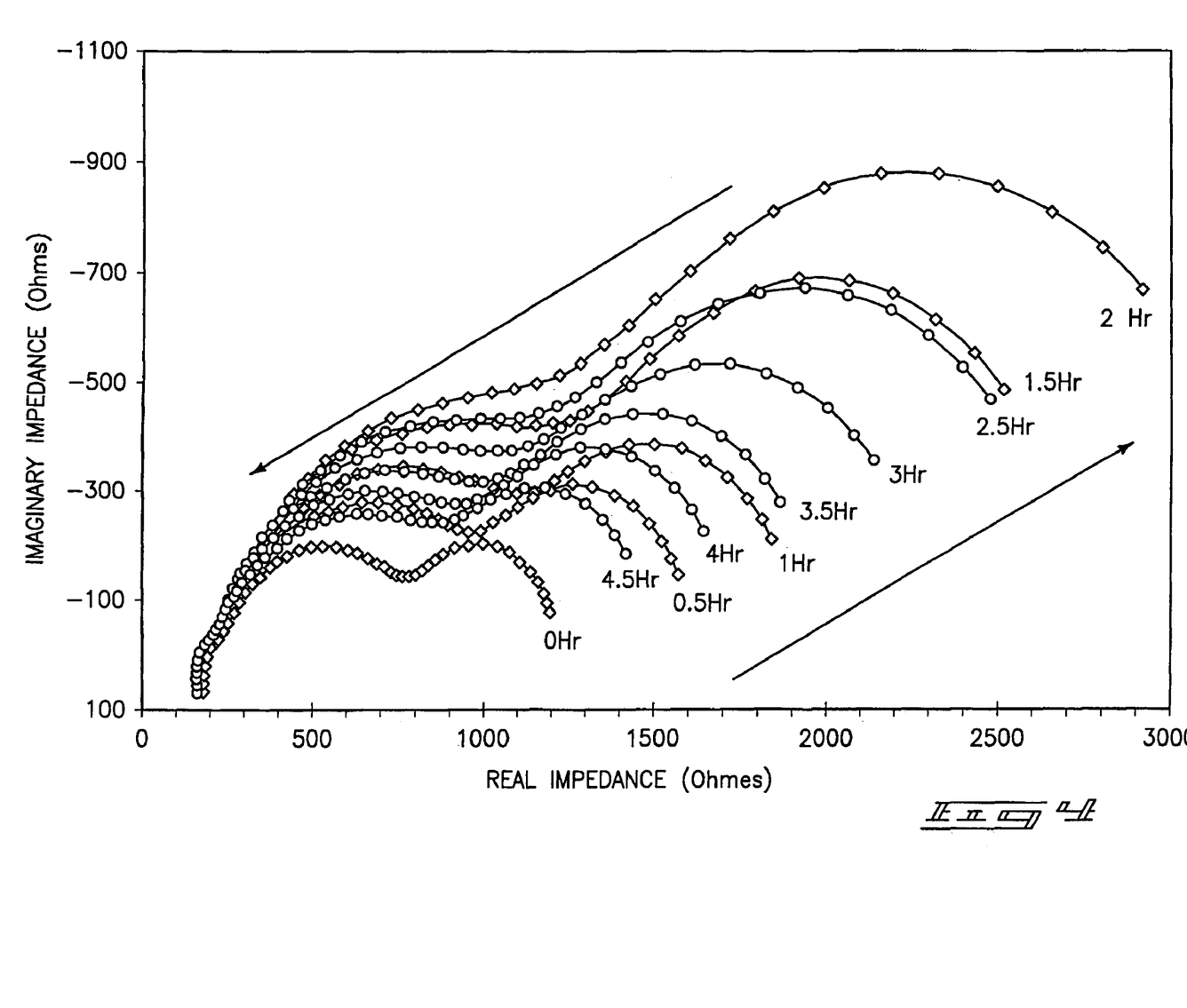
FIG. 4 shows a representative electrochemical impedance spectroscopy plot during curing process of a concrete material sample in accordance with one embodiment of the invention.

FIG. 4 shows a representative electrochemical impedance spectroscopy plot during curing process of a concrete material sample in accordance with one embodiment of the invention. In one example, the sample 102 (FIG. 1A) can be uncured concrete material. As illustrated in FIG. 4, the inventors have observed that the impedance of the concrete material sample increases for the first two hours of curing of the concrete material and decreases thereafter. Such measured data and the impedance spectra can be used to monitor the curing process of the concrete material sample.

FIG. 5 shows a representative impedance plot for different sections of a concrete material sample to detect differences in gravel concentration in fully cured concrete in accordance with one embodiment of the invention. In one case, the sample 102 (FIG. 1A) can be a solid concrete slab. As illustrated in FIG. 5, the inventors have observed that electrochemical impedance spectroscopy can be used to detect differences in gravel concentration in fully cured concrete.

Figure 6:
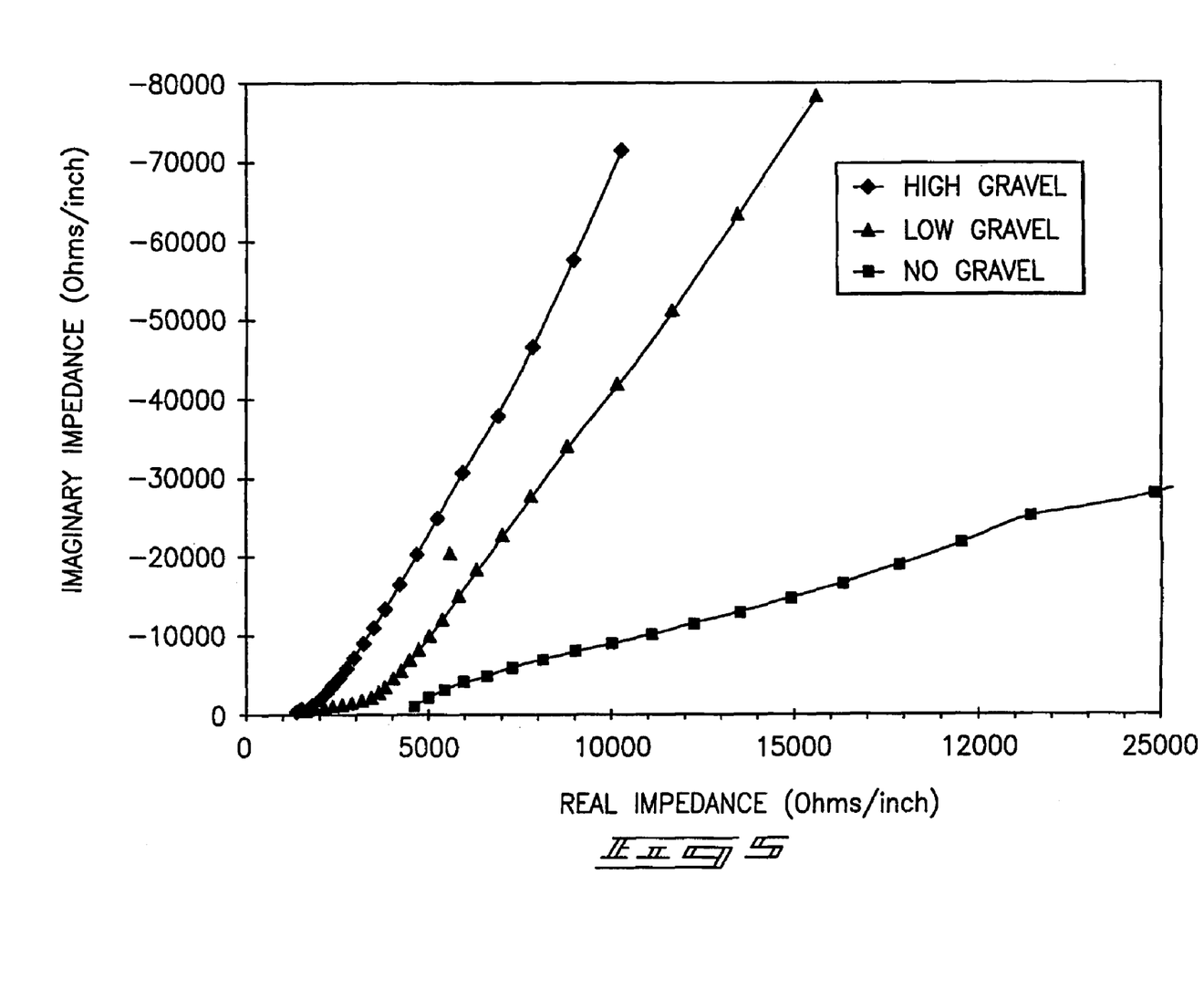
FIG. 6 shows a representative graph to detect water intrusion into cured concrete in accordance with one embodiment of the invention.

FIG. 6 shows a representative graph to detect water intrusion into cured concrete in accordance with one embodiment of the invention. The inventors have added water to a material sample (e.g., concrete slab or sample 102 of FIG. 1A) and monitored the impedance of the sample at a frequency (e.g., 10 kHz) over a period of time. The inventors have observed that water intrusion can be detected in roads and bridge structures by monitoring the impedance measurements.

Figure 7:
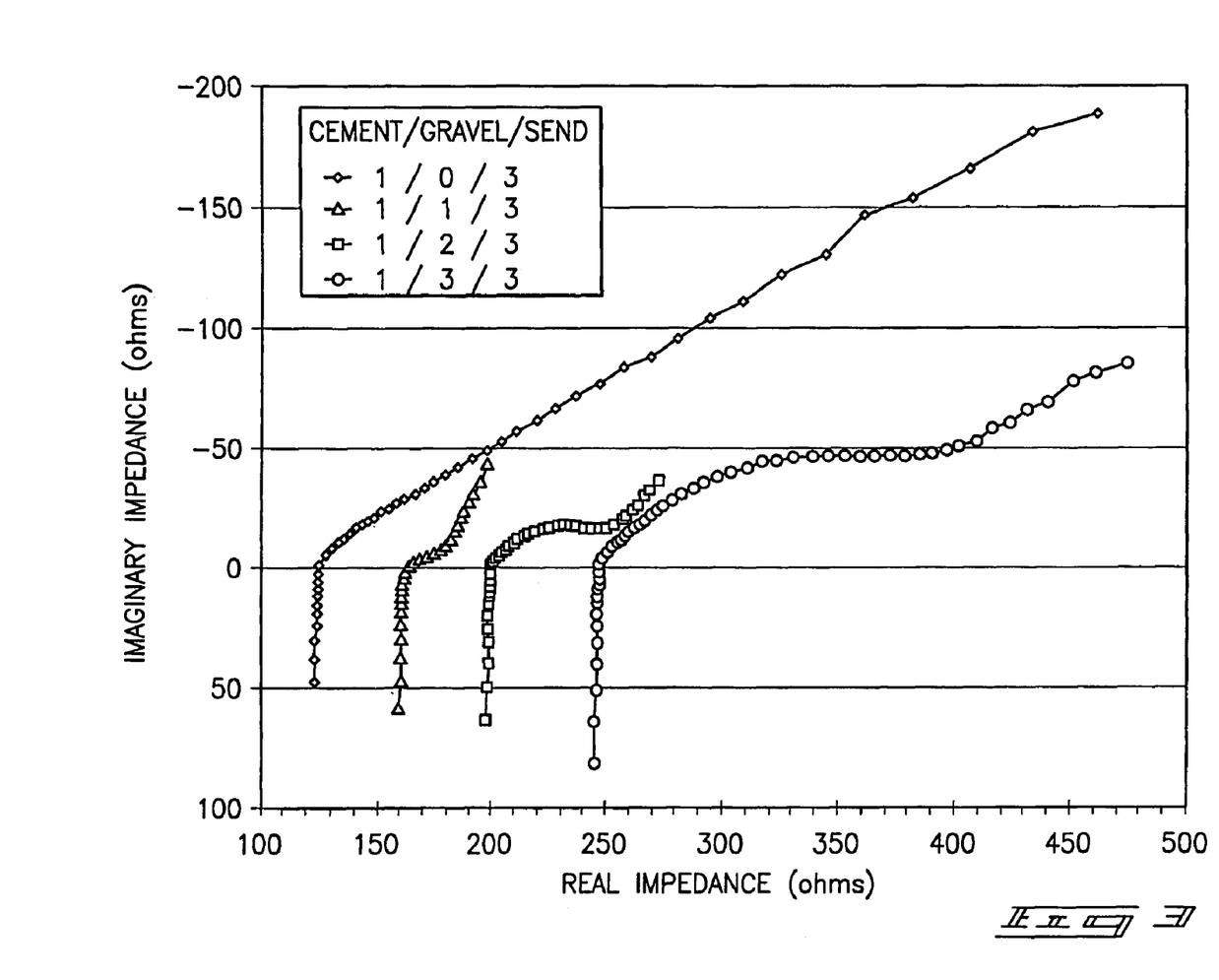
FIG. 7 shows a representative graph to determine the weight of an object placed on a concrete material sample in accordance with one embodiment of the invention.

FIG. 7 shows a representative graph to determine the weight of an object placed on a concrete material sample in accordance with one embodiment of the invention. A series of weights are placed on the concrete material sample (e.g., sample 102 of FIG. 1A) and impedance values of concrete material sample at a predetermined frequency (e.g., 1000 Hz) are measured for individual ones of the weights on the sample. The measured impedance values are compared with known impedance values of the sample with weights placed thereon. The inventors have observed that when weights are removed from the sample, the impedance values of the sample return to a steady state condition (e.g., impedance values without the added weight). Accordingly, the inventors have determined that by placing a plurality of electrodes (e.g., electrodes 104, 106 of FIG. 1A) on either sides of a concrete highway or roadway, the number of vehicles passing a given point on the highway can be determined. The inventors have also observed that the weight of vehicles on the highway can be determined without the need for expensive weighing scales. The inventors have also determined that using electrochemical impedance spectroscopy as described with respect to FIG. 1A, it is possible to (a) determine the speed of a vehicle passing a section of a known length of a highway, and (b) monitor the progressive damage caused to the concrete highway by heavy vehicles.

EXAMPLE 1

In some embodiments, electrochemical impedance spectroscopy can be used to determine spatial locations of defects in a material using a system as shown in FIG. 1A. The method includes providing a plurality of electrodes 104, 106 in contact with a material (e.g., sample 102), and applying a sinusoidal voltage to a select number of the electrodes 104 at a predetermined frequency. Gain and phase angle measurements are determined at other of the electrodes 106 in response to applying the sinusoidal voltage to the select number of electrodes. Impedance values are determined from the gain and phase angle measurements using the processing circuitry 112. An impedance spectrum is computed, using processing circuitry 112, for an area of the material (e.g., sample 102) from the determined impedance values, and the computed impedance spectrum is compared with a known impedance spectrum to identify spatial locations of defects in the material. The material can be concrete (e.g., wet, dry, cured, uncured). The defects include voids present in the material, separation of the material from a reinforcing bar, intrusion of moisture into the material, micro-cracking of the material, and freeze-thaw damage of the material.

A system for performing the task of Example 1 as described above includes a plurality of electrodes 104, 106

(FIG. 1A), a voltage source 108, and an output measuring device 110 (e.g., current measuring device). The system also includes a processing circuitry 112 configured to perform the various tasks associated with determining spatial locations of defects in a material as described above.

EXAMPLE 2

In other embodiments, electrochemical impedance spectroscopy can be used to monitor the stability of a bridge structure. The method includes providing a plurality of spaced apart electrodes 104, 106 (FIG. 1A) in contact with the bridge structure, applying a voltage to a select number of the electrodes 104, the voltage being applied at a predetermined frequency. A current response is measured (e.g., using output measuring device 110) at other of the electrodes 106 in response to applying the voltage. The processing circuitry 112 can be used to determine impedance measurements by using the applied voltage and the measured current response. An impedance spectrum is computed from the impedance measurements. The computed impedance spectrum can be analyzed, either manually or automatically using the processing circuitry 112, relative to a known impedance spectrum to identify defects of the bridge structure so as to determine the stability of the bridge structure. Components of the system shown and described in FIG. 1A can be used to monitor the stability of the bridge structure.

EXAMPLE 3

In other embodiments, electrochemical impedance spectroscopy can be used to determine the weight of an object after placing the object on a concrete structure (e.g., sample 102). A plurality of spaced apart electrodes 104, 106 (FIG. 1A) are provided in contact with the concrete structure. A sinusoidal voltage is applied to select ones of the electrodes 104 at a predetermined frequency and a current response is measured at other of the electrodes 106 in response to applying the sinusoidal voltage. Impedance measurements, of the concrete structure with the object on the concrete structure, are made using the applied sinusoidal voltage and the measured current response. An impedance spectrum is computed from the impedance measurements. The impedance spectrum is analyzed with known impedance spectra for differing weights to determine the weight of the object provided on the concrete structure. Such can be either performed by manually comparing the impedance spectra or it can be automatically performed by the processing circuitry 112. The storage device 206 (FIG. 2) can be stored with a plurality of impedance spectra of the concrete sample (e.g., sample 102) corresponding to various weights placed on the concrete sample. The computed impedance spectrum can be compared with the stored impedance spectra, and a determination can be made regarding the weight of the object received on the concrete sample.

EXAMPLE 4

In further embodiments, electrochemical impedance spectroscopy can be used to determine the speed of a vehicle. The vehicle can be made to pass on a given length of a concrete sample (e.g., sample 102 of FIG. 1A). A first pair of spaced apart electrodes (e.g., one of the electrodes 104 and one of the electrodes 106) is configured to contact the concrete structure at a first location (e.g., a first end of the sample 102 of predetermined length). For example, of the first pair of electrodes, one electrode can be considered to be one of the electrodes 104 and the other of the electrodes can be considered to be one of the electrodes 106, shown to be directly across the electrode 104 in FIG. 1A.

A second pair of spaced apart electrodes (e.g., another of the electrodes 104 and 106) is configured to contact the concrete structure at a second location (e.g., another end opposite to the one end of the sample 102). A sinusoidal voltage is applied to one of the electrodes of both the first and second pairs of electrodes at a predetermined frequency. The vehicle is caused to move on the concrete structure between the first and second ends. Impedance measurements are made at the first and second locations of the concrete structure and in response to applying the sinusoidal voltage. The measured impedance values are compared with known impedance measurements of the concrete structure without the vehicle moving on the concrete structure, and the impedance variations at the first and second locations are determined from the comparison. A first and second time instants are recorded for the monitored impedance variations at the first and second locations, respectively, and an elapsed time period between the first and second time instants is determined. The speed of the vehicle is computed using the elapsed time period and the predetermined distance between the first and second locations.

Other applications of the electrochemical impedance spectroscopy can include, for example, measuring the extent of earthquake damage in concrete slabs in buildings, highways, bridges, continuous monitoring of nuclear reactor containment of vessels for structural integrity, continuous monitoring of loading on concrete slabs (e.g., parking garages), quality control of fresh concrete, locating voids and cracks in cured concrete, and determining the extent of corrosion in reinforcing steel.

Electrochemical impedance spectroscopy can be advantageously used as a tool for investigating the properties of materials. A direct relationship exists between a real system and that of an idealized model circuit consisting of discrete electrical components. The impedance of an analog circuit model having, for example, resistors, capacitors, and inductors, can approximate the experimental impedance data. In such a circuit, a resistance can represent a conductive path and a given resistor in the circuit can account for the bulk conductivity of the material or one step in a chemical reaction at the metal-solution interface. Capacitances and inductances are generally associated with space charge polarization. Changes in the magnitude of the various resistors, inductances, and capacitances, over time can reflect changes in specific properties of the materials being measured.

Electrochemical impedance spectroscopy techniques can provide a way to monitor the curing process and long term performance of cement structures, and could provide a simple, inexpensive method to determine the relative permeability, stability, and durability of cementitious systems. Electrochemical impedance spectroscopy can also be used for jet grouting.

Electrochemical impedance spectroscopy has the potential to measure or indicate for various physical and chemical properties of materials including (a) measuring the size and content of aggregate in concrete prior to, during, and after curing, (b) detecting voids and cracks in concrete and other solid matrices, (c) measuring the bulk conductivity of monolithic structures, and (d) identifying regions of reactivity in solid phase reactive media such as, for example, as used in permeable reactive barriers.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of determining defects in uncured concrete, prior to curing of the concrete, comprising:
   providing a plurality of electrodes in contact with the uncured concrete;
   applying a sinusoidal voltage to a select number of transmitting electrodes for each of a plurality of source signal frequencies;
   determining gain and phase angle measurements at receiving electrodes in response to applying the sinusoidal voltage to the select number of electrodes;
   determining impedance values from the gain and phase angle measurements;
   computing an impedance spectrum for an area of the uncured concrete from the determined impedance values; and
   comparing the computed impedance spectrum with a known impedance spectrum to identify of defects in the uncured concrete, wherein defects in the uncured concrete can be rectified before the concrete cures.

2. The method of claim 1, further comprising displaying the spatial locations of the identified defects.

3. The method of claim 1, wherein shape and slope of the impedance spectrum is related to physical and chemical characteristics of the uncured concrete.

4. The method of claim 1, wherein the predetermined frequency is selected from a range of about 1 MHz to about 10 MHz.

5. The method of claim 1, wherein the spatial locations of the defects are determined by identifying a variation in impedance value in the computed impedance spectrum relative to a known impedance value of the known impedance spectrum.

6. The method of claim 1, wherein the defects that can be determined include voids present in the material.

7. The method of claim 1 and further comprising determining a composition of a concrete material, wherein comparing the computed impedance spectrum comprises
   comparing the computed impedance spectrum with a known impedance spectrum to determine percentages of concrete, sand, gravel, and water in the concrete material.

8. The method of claim 7, further comprising displaying the composition of concrete material using at least one of a graphical representation and a textual representation.

9. The method of claim 8, wherein shape and slope of the impedance spectrum is related to physical and chemical characteristics of the concrete material.

10. The method of claim 7, wherein the predetermined frequency is selected from a range of about 1 MHz to about 10 MHz.

11. A system for determining the presence of defects in uncured concrete, comprising:
    a plurality of electrodes configured to be placed in contact with the uncured concrete, the plurality of electrodes being spaced from each other;
    a voltage source configured to apply a sinusoidal voltage to a select number of transmitting electrodes for each of a plurality of source signal frequencies;
    a current measuring device coupled to receiving electrodes to measure a current response in response to applying the sinusoidal voltage; and
    a processor configured to:
       determine impedance measurements using the applied sinusoidal voltage and the measured current response;
       compute an impedance spectrum from the impedance measurements; and
       compare the impedance spectrum with a known impedance spectrum to identify defects in the concrete before the concrete cures.

12. The system of claim 11, wherein the processor is further configured to display the spatial locations of the identified defects.

* * * * *